US00PP26401P2

(12) United States Plant Patent
Bernabe

(10) Patent No.: US PP26,401 P2
(45) Date of Patent: Feb. 2, 2016

(54) ***SALVIA* PLANT NAMED 'RED SWING'**

(50) Latin Name: ***Salvia* hybrid**
Varietal Denomination: Red Swing

(71) Applicant: Catherine Bernabe, El Campello (ES)

(72) Inventor: Catherine Bernabe, El Campello (ES)

( * ) Notice: Subject to any disclaimer, the term of this patent is extended or adjusted under 35 U.S.C. 154(b) by 158 days.

(21) Appl. No.: 13/998,089

(22) Filed: Sep. 30, 2013

(51) Int. Cl.
*A01H 5/02* (2006.01)

(52) U.S. Cl.
USPC ..... Plt./475

(58) Field of Classification Search
USPC ..... Plt./475
See application file for complete search history.

(56) References Cited

PUBLICATIONS

McHutchison Florexpo Unrooted Cuttings 2012-2013 retrieved on May 14, 2015, retrieved from the Internet at <http://mchutchison.com/McH_Florexpo_12-13.pdf> pp. 1-3, 29 and 98-100.*
Appleby. Horticulture Week. Nurseries buoyed by sales pick-up ahead of National Plant Show Jun. 21, 2013, retrieved on May 14, 2015, retrieved from the Internet at <http://www.hortweek.com/nurseries-buoyed-sales-pick-up-ahead-national-plant-show/article/1186669> pp. 1-9.*
New Plants and Flowers Jun. 1, 2012, retrieved on May 19, 2015, retrieved from the Internet at <http://www.newplantsandflowers.com/french-salvia-hybrids-on-dutch-trade-fair/> 2 pp.*

* cited by examiner

*Primary Examiner* — June Hwu
(74) *Attorney, Agent, or Firm* — Penny J. Aguirre

(57) ABSTRACT

A new cultivar of hybrid *Salvia*, 'Red Swing', that is characterized by its compact, shrubby plant habit, its curly leaves, and its fragrant red flowers with purple-black calyces on dark colored flowering stems.

2 Drawing Sheets

Botanical classification: *Salvia* hybrid.
Variety denomination: 'Red Swing'.

BACKGROUND OF THE INVENTION

The present invention relates to a new and distinct cultivar of *Salvia* of hybrid origin and will be referred to hereafter by its cultivar name, 'Red Swing'. 'Red Swing' is an herbaceous perennial grown for landscape use.

The new *Salvia* resulted from a controlled breeding program conducted by the Inventor in Henansal, France. The Inventor made crosses in 2008 between unnamed proprietary plants of interspecific hybrid origin (*Salvia chamaedryoides*× *Salvia lycoides*) in the Inventor's breeding program as both the female and male parents. The characteristics of the parents are unknown as seeds where pooled and sown from several crosses. 'Red Swing' was selected as a single unique plant in 2008 from the resulting seedlings of the above crosses.

Asexual propagation of the new cultivar was first accomplished by the Inventor by vegetative stem cuttings in 2009 in Henansal, France. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Red Swing' as a unique cultivar of *Salvia*.

1. 'Red Swing' a compact, shrubby plant habit.
2. 'Red Swing' exhibits curly leaves.

3. 'Red Swing' exhibits fragrant red flowers with purple-black calyces on dark colored flowering stems.

'Red Swing' can also be most closely compared to the *Salvia* cultivar 'Royal Bumble' (not patented) and typical plants of the species *Salvia microphylla*. 'Royal Bumble' differs from 'Red Swing' in being less compact and less shrubby in plant habit. Typical plants of *Salvia microphylla* differs from 'Red Swing' in being less compact and in having flowers that are lighter red in color.

BRIEF DESCRIPTION OF THE DRAWING

The accompanying colored photographs illustrate the overall appearance and distinct characteristics of a one year-old plant of the new *Salvia* as grown in a greenhouse in Henansal, France (dug for the photograph).

The photograph in FIG. 1 provides a side view of 'Red Swing' in bloom.

Figure 1:
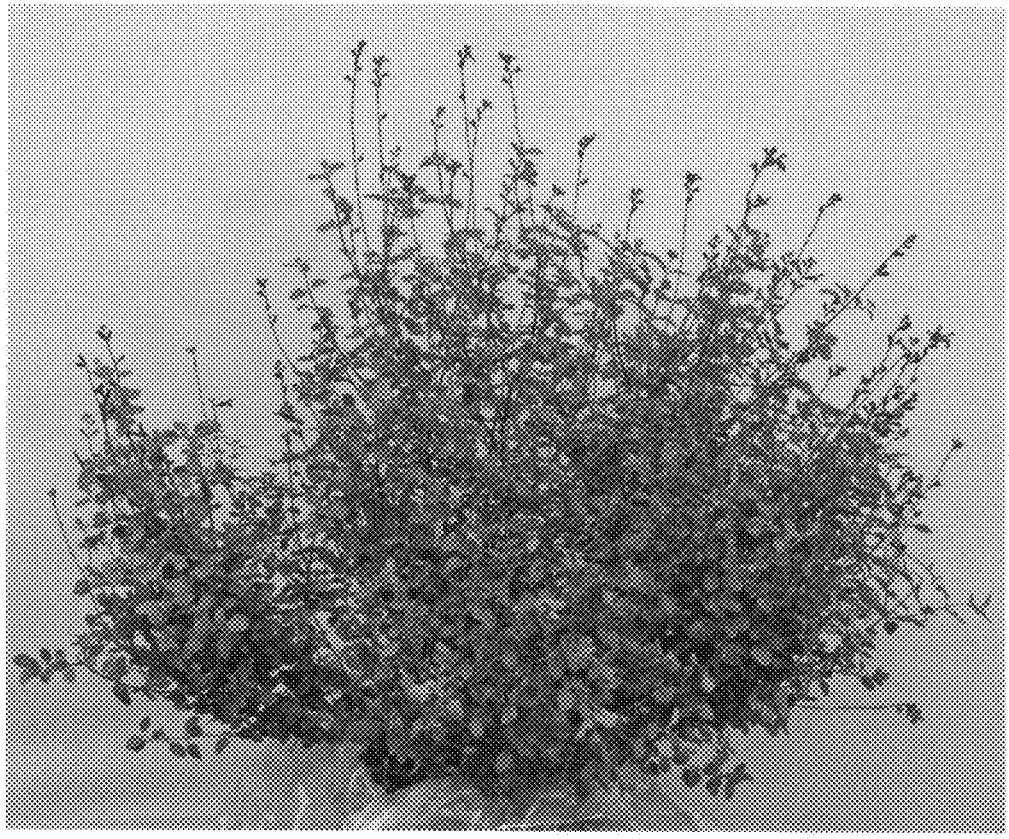
Figure 2:
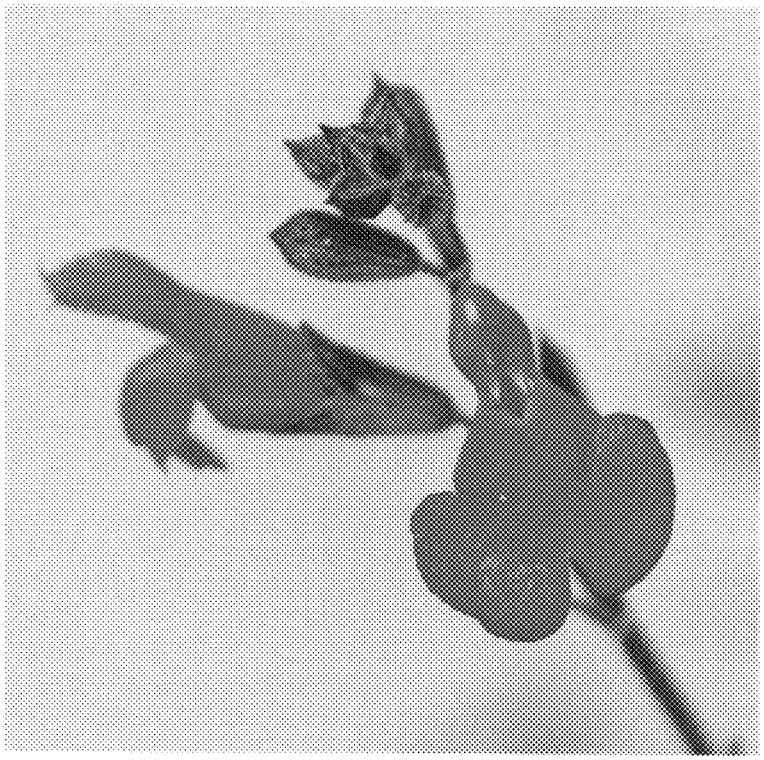

The photograph in FIG. 2 provides a close-up view of the flowers of 'Red Swing'.

Figure 3:
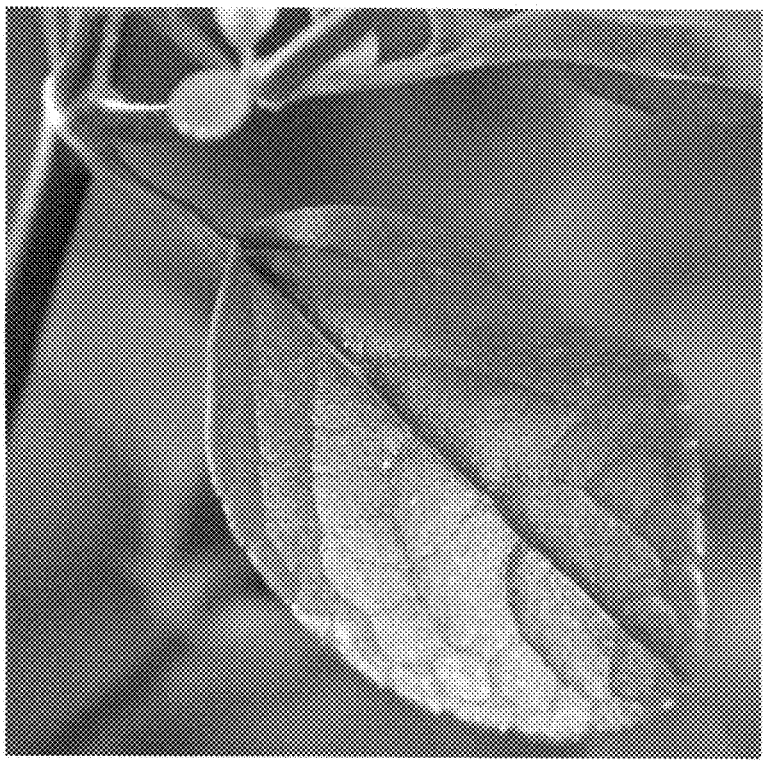

The photograph in FIG. 3 provides a close-up view of a leaf of 'Red Swing'.

The colors in the photographs may differ slightly from the color values cited in the detailed botanical description, which accurately describe the colors of the new *Salvia*.

DETAILED BOTANICAL DESCRIPTION

The following is a detailed description of three year-old plants of 'Red Swing' as grown in a greenhouse in Henansal, France. Plants were grown under average day temperatures ranging from +14° to +30° C. and average night temperatures of +8° to +18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—May to first frost in Henansal, France.

*Plant type*.—Herbaceous perennial.

*Plant habit*.—Broadly upright, shrubby, compact.

*Plant size*.—Reaches up to 78.4 cm in height and 91.5 cm in spread.

*Cold hardiness*.—At least in U.S.D.A. Zone 8.

*Diseases and pests*.—No susceptibility or resistance to diseases or pests have been observed.

*Root description*.—Fibrous, non-spreading.

*Propagation*.—Vegetative stem cuttings.

*Growth rate*.—Moderate to vigorous.

Stem description:

*Shape*.—Quadrangular.

*Stem color*.—187C on upper side, 146B to 146C on lower side.

*Stem size*.—Average of 17.1 cm in length and 2 mm in diameter.

*Stem surface*.—Moderately glossy and densely covered with very short soft hairs; average of 0.2 mm in length and 156D in color.

*Stem fragrance*.—When rubbed the leaves give a "sage" like fragrance.

*Internode length*.—Average of 3.4 cm.

*Branching*.—Average of 27 main stems, an average of 10 lateral braches per main stem.

Foliage description:

*Leaf shape*.—Broadly ovate.

*Leaf division*.—Simple.

*Leaf base*.—Obtuse.

*Leaf apex*.—Obtuse.

*Leaf fragrance*.—When rubbed the leaves give a "sage" like fragrance.

*Leaf venation*.—Pinnate, upper surface is 138B in color, lower surface is 138A in color.

*Leaf margins*.—Crenate.

*Leaf arrangement*.—Opposite.

*Leaf attachment*.—Petiolate.

*Leaf aspect*.—Curly.

*Leaf surface*.—Slightly rugose and dull on both surfaces.

*Leaf size*.—Up to 2.3 cm in length and 1.6 cm in width.

*Leaf color*.—Young leaves; upper surface 143A, lower surface 143B, mature leaves; upper surface a color between 137B and 143A, lower surface 138A.

*Leaf quantity*.—Average of 12 (6 pairs).

*Petioles*.—Up to 0.7 cm in length and 1 mm in diameter, 143D in color.

Inflorescence description:

*Inflorescence type*.—Terminal verticillaster, individual flowers are in whorls of 2.

*Lastingness of inflorescence*.—Approximately 5 days.

*Inflorescence size*.—An average of 16.5 cm in height and 3.4 cm in width.

*Flower type*.—Labiate.

*Flower number*.—An average of 18 per vertillicaster (9 pairs).

*Flower fragrance*.—Sage scented.

*Flower buds*.—Obovate in shape, about 1 cm in length and 4 mm in diameter, color; upper side to back side is a blend of N186A and 203A, under side is 143B, top (immature petals) is 59A to 59B.

*Flower size*.—About 2.2 cm in depth and about 1.4 cm in width (horizontal) and 1.7 cm in height (vertical).

*Peduncle*.—An average of 15.9 cm in length and 1.5 mm in width, held straight on top of lateral branch, strong in strength, color; 144A and tinged with N186A and 203A.

*Pedicels*.—About 4 mm in length and 0.75 mm in diameter, held at an average angle of 25°, strong in strength and a color between N186A and 203A in color.

*Calyx*.—Campanulate in shape, average of 1 cm in length and 4 mm in width.

*Sepals*.—3, campanulate in arrangement, narrow obovate in shape with lower 70% fused, entire margin, acute apex, cuneate base fused into tube, surface is dull and covered with very short glandular hairs, average of 0.4 mm in length and 186C to 186D in color, average of 1 cm in length and 3.5 mm in width, color: immature upper (inner) side; 146A, striped with 200B to 200C, under side is 144B and striped 146A, immature lower (outer) side; upper side between N186A and 203A, under side is 143B, mature upper (inner) side; 146A, striped 200B to 200C, under side 144B and striped 146A, mature lower (outer) side; a color between N186A and 203A, under side 143B.

*Petals*.—2, labiate, arranged in 2 lips, lower 65% fused into tube at base, upper lip; broad elliptic and folded in shape, upper lip; broadly elliptic in shape and folded, entire margin, retuse apex, 2.2 cm in length and 3 mm in width, lower lip; spathulate in shape and 2 lobed, margin is 2 lobed, emarginated apex, 2.3 cm in width and 1.4 cm in length, tube; 1.1 cm in length and 3 mm in width, color of upper and lower lips: when opening upper (inner) side; upper and lower lip 45A, inside of tube is N57A, when opening lower (outer) side; 46B, top of upper part of petal is 53B, when fully open upper (inner) side; upper and lower lip 45A, inside of tube is N57A, when fully open lower (outer) side; upper and lower lip , top of upper part of petal is 53B.

Reproductive organs:

*Gynoecium*.—1 pistil, about 2.2 cm in length, style is 2 cm in length and NN155D in color, stigma is cleft (2 parted) and N57B to N57C in color, ovary is 145D in color.

*Androcoecium*.—2 stamens, filaments are N157C in color and 1.1 cm in length, anthers are dorsifixed and narrowly elliptic in shape, an average of 1.5 mm in length and 26C in color, pollen is moderate in quantity and 17A to 17B in color.

*Fruit and seed*.—Observed to be sterile with no viable seeds formed.

It is claimed:

1. A new and distinct cultivar of *Salvia* plant named 'Red Swing' as herein illustrated and described.

* * * * *